United States Patent [19]

Koyama et al.

[11] Patent Number: 4,522,725
[45] Date of Patent: Jun. 11, 1985

[54] PROCESS FOR SEPARATING PLASMA ALBUMIN

[75] Inventors: Kenji Koyama; Syotaro Ohno, both of Tokuyama; Mitsutoshi Fukuda, Shin-nanyo, all of Japan

[73] Assignee: Toyo Soda Manufacturing Co., Ltd., Shin-nanyo, Japan

[21] Appl. No.: 204,717

[22] Filed: Nov. 6, 1980

[30] Foreign Application Priority Data

Jan. 10, 1980 [JP] Japan ............................ 55-855

[51] Int. Cl.$^3$ ............................................. B01D 13/00
[52] U.S. Cl. ....................................... 210/639; 210/651
[58] Field of Search ............ 210/927, 651, 634, 490, 210/500.2; 55/16

[56] References Cited

U.S. PATENT DOCUMENTS

| 3,615,024 | 10/1971 | Michaels | 210/490 |
| 3,691,068 | 9/1972 | Cross | 210/500.2 X |
| 4,087,415 | 5/1978 | Bick et al. | 210/927 X |
| 4,157,960 | 6/1979 | Chang et al. | 55/16 X |

OTHER PUBLICATIONS

Michaels, "New Separation Technique for the CPI", from Chem. Eng. Progress, vol. 64, No. 12, Dec. 1968, pp. 31–43.

Porter et al., "Membrane Ultrafiltration", from Chem. Tech., 1-1971, pp. 56–63.

Primary Examiner—Frank Spear
Attorney, Agent, or Firm—Oblon, Fisher, Spivak, McClelland & Maier

[57] ABSTRACT

Plasma albumin is separated by a crude albumin fraction from blood plasma by a rough fractional separation and then separating plasma albumin through an ultrafiltration membrane. The ultrafiltration membrane is a membrane made of a polysulfone resin having the formula

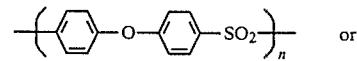 or

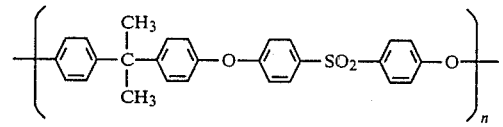

(n=50 to 250).

4 Claims, 3 Drawing Figures

PROCESS FOR SEPARATING PLASMA ALBUMIN

BACKGROUND OF THE INVENTION

1. Field of the Invention

The present invention relates to a plasma albumin medicine. More particularly, it relates to a process for separating a substantially pure plasma albumin from blood plasma.

2. Description of the Prior Arts

Recently, blood has been used for not only the blood transfusion for the emergency life saving but also the blood storage and the preparation of blood medicines. Because of such technical development, only the important blood component is separated and transfused whereby it is possible to administrate at a desired dose and to prevent side-effects caused by needless components and to effectively utilize human blood which is the important minor source.

It has been well-known that blood can be separated into erythrocyte, leukocyte, blood platelets, and liquid blood plasma. The blood plasma contains various proteins which have different functions. It is desirable that the proteins of blood plasma are separated and purified and only desired component fraction is used depending upon the purpose. Among the proteins of blood plasma, plasma albumin has function for maintaining osmotic pressure of blood, and transferring biologically indispensable materials such as nutrition to various organs.

The medical applications of plasma albumin include therapy for hypoalbuminemia and edema caused by hypoalbuminemia; emergency therapy for hemorrhagic shock or burns and removement of plasma bilirubin in exchange transfusion of new born, etc. Excellent results have been attained in these applications.

As processes for separating plasma albumin from blood plasma, it has been known to utilize difference of solubilities of molecules difference of charges and sizes of molecules as follows:

(1) a fractional precipitation by addition of a neutral salt such as ammonium sulfate; or an organic solvent such as cold ethanol or a water soluble macromolecule such as polyethyleneglycol;

(2) a chromatography using an ion exchanger or an adsorbent or a molecular seive etc.;

(3) an electrophoretic process based on difference of charges;

(4) an immunoadsorption.

The above-mentioned process or combination thereof has been employed. These processes have disadvantages to cause damage of structure of the plasma protein molecule by the operation at room temperature; to form aggregate; to require a long time for separation or a precise operation.

SUMMARY OF THE INVENTION

It is an object of the present invention to a process for separating plasma albumin by simple operation for a short time without breaking the structure of plasma protein nor forming aggregate.

The foregoing and other objects of the present invention have been attained by separating a crude albumin fraction from blood plasma by a rough fractional separation and then separating plasma albumin through an ultrafiltration membrane made of a polysulfone resin.

DETAILED DESCRIPTION OF THE PREFERRED EMBODIMENTS

Figure 1:
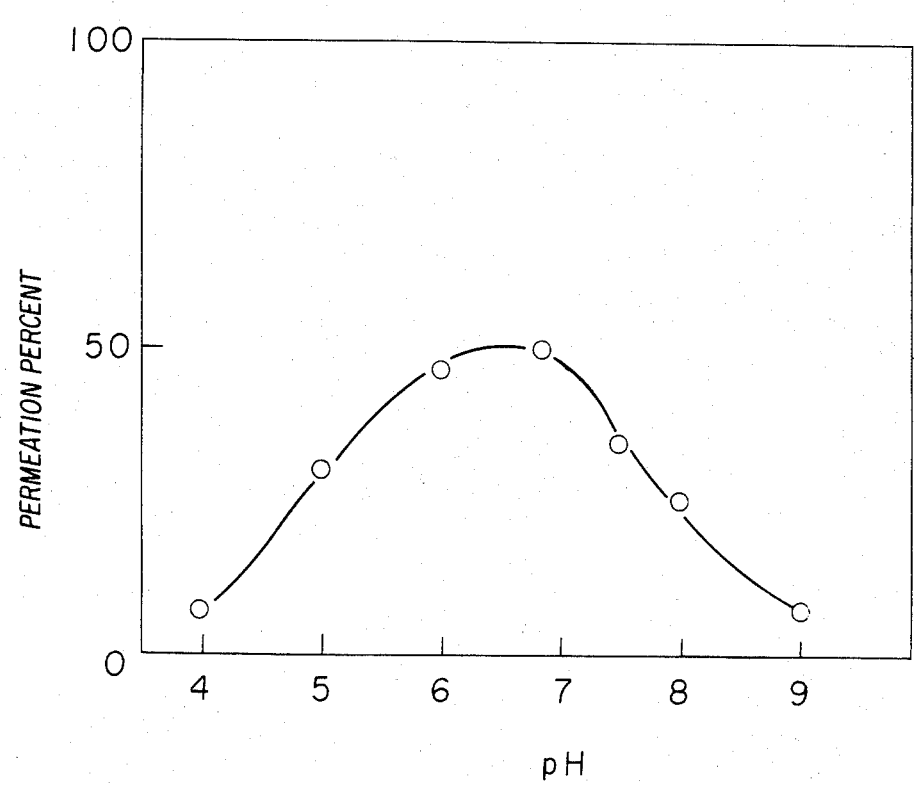
FIG. 1 shows the relation of permeation percent of albumin and pH of solutions in the cases using the same membrane and the same sample as those of Example 1.

The inventors have studied the improvement for the known technology from different viewpoints and have found novel process for separating plasma albumin from blood plasma.

In accordance with the process of the present invention, a crude albumin fraction is separated by a fractionation of blood plasma with a precipitating agent such as water soluble macromolecular compounds, neutral salts and cold ethanol, and the crude albumin fraction is treated by an ultrafiltration with an ultrafiltration membrane under the condition permeating only pure plasma albumin, whereby plasma albumin is separated for a short time by simple operation.

The crude albumin fraction in the present invention means a fraction of plasma albumin which does not substantially contain $\gamma$-globulin (molecular weight of $16\times 10^4$) such as a crude albumin fraction obtained by fractionation with polyethyleneglycol and $S_{II+III}$ fraction obtained by cohn fractionation with cold ethanol. When the fraction contains $\gamma$-globulin, $\gamma$-globulin also permeate together with plasma albumin through the ultrafiltration membrane whereby a pure plasma albumin can not be obtained. The process for fractionating the crude albumin fraction is not critical and is not limited to the above-mentioned process.

When blood plasma is directly treated by an ultrafiltration, fibrinogen in the blood plasma is adsorbed on the ultrafiltration membrane whereby the ultrafiltration of plasma albumin is disadvantageously slow. In order to overcome these disadvantages fibrinogen is previously separated by a fractionation with polyethyleneglycol, a neutral salt etc. and then, the resulting crude albumin fraction is treated by the ultrafiltration membrane to obtain a pure plasma albumin. The process of the present invention has been completed by the finding.

As the ultrafiltration membrane used in the process of the present invention, a membrane made of polysulfone resin having the following unit structure is preferably used.

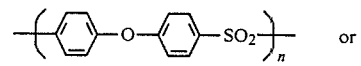 or

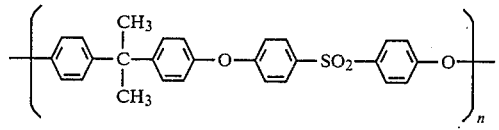

(n=50 to 250)

The membrane can be prepared by dissolving the polysulfone in a solvent and then, the solution is spread in a form of a film and is immersed into a non-solvent.

The pore diameter of the membrane can not be observed by an electron microscope. In the case of the ultrafiltration membrane, it is usual to define the property of a membrane by a cut-off molecular weight.

A cut-off molecular weight is usually defined by measuring retention percents of the membrane with a spherical protein having the known molecular weight (1-concentration of permeated solution/concentration of original solution)×100 and plotting the molecular weights of the solute and the retention percents and calculating the molecular weight at the retention percent of 100%. The cut-off molecular weight may be varied depending upon the process of measurement. For example, PM-10 membrane manufactured by Amicon Co. is referred as a cut-off molecular weight of 10,000, however, myoglobin having a molecular weight of 18,000 is permeated through the membrane. The cut-off molecular weight is varied depending upon the process for measurement. For example, the cut-off molecular weight is varied depending upon the variation of pH of the solution even though the sample and the membrane are the same. The variation is considered depending upon charges of the protein and distribution of the protein in the solution.

In this case, the cut-off molecular weight is determined by using proteins having known molecular weights (myoglobin, $\beta$-lactoglobulin, albumin, $\gamma$-globulin etc.) in a phosphate buffer solution (pH: 6.8) as an elute of an aqueous gel permeation chromatography (GPC), measuring ratios of absorbance of the sample at 280 nm by G3000SW column manufactured by Toyo Soda Mfg. Co. and plotting the retention percents of the membrane. In the present invention, the cut-off molecular weight at pH of 6.8 is shown.

The cut-off molecular weight of the ultrafiltration membrane used in the present invention is usually in a range of $2 \times 10^5$ to $3.5 \times 10^5$ preferably $2.5 \times 10^5$ to $3 \times 10^5$. The process for measuring the retention percent is not limited to the process of the present invention.

Among ultrafiltration membranes having the same cut-off molecular weight, membranes made of a polyamide, a polyethyleneterephthalate, a polycarbonate, cellulose or cellulose acetate, sometimes permeate macromolecular proteins as well as albumin or the permeation percent of plasma albumin is remarkably low to be inferior separatability. For example, when a cellulose membrane is used, the proteins adsorbed on the membrane to be remarkably lower ultrafiltration rate. On the contrary, when a polysulfone resin membrane is used, an ultrafiltration membrane having remarkably narrow distribution of pore diameters can be obtained to give a constant ultrafiltration rate without any adsorption of the proteins on the membrane. This is the optimum membrane for separating plasma albumin. Therefore, it has been possible to separate the components depending upon difference of sizes as the feature of ultrafiltration membrane. Thus, the ultrafiltration has been attained by a simple and speedy process depending upon difference of sizes of plasma albumin and the other proteins.

In the separation with the membrane, pH of the aqueous solution is preferably in a range of 5 to 8 especially 6 to 7.5. The permeation percent of plasma albumin (concentration of permeated solution/concentration of original solution×100) is remarkably varied depending upon pH.

FIG. 1 shows the relation of permeation percent of plasma albumin and pH of the solution. The time for treatment can be shorter depending upon higher permeation percent. In view of the economical problem, the optimum pH in the separation with the membrane is preferably in a range of 5 to 8 especially 6 to 7.5. The concentration of the solution is preferably lower than 2% (W/V). When it is higher, the ultrafiltration rate is lower and the permeation percent of plasma albumin is lower, because a concentration polarization of the solute on the surface of the membrane is higher.

In accordance with the process of the present invention, the pH of the aqueous solution of the crude albumin fraction is adjusted in a range of 5 to 8. The ultrafiltration of the solution through the membrane is carried out to retain the other proteins on the membrane and to permeate plasma albumin through the ultrafiltration membrane. Then, the plasma albumin solution permeated can be treated by steps of concentrating with a membrane and desalting.

The process of the present invention can be applied not only for the blood plasma derived from human but also for the blood plasma derived from animals such as cattle, horse and sheep.

The present invention will be illustrated by certain examples and references which are provided for purposes of illustration only and are not intended to be limiting the present invention.

EXAMPLE 1

A polycondensate of diphenylsulfone and bisphenol-A (n=170) was dissolved in dimethylacetamide to prepare 12% (W/V) solution. The solution was spread on polyethylene non-woven fabric having a size of 30 cm×30 cm to be a thickness of 200$\mu$ by a doctor-knife and was immersed into water to obtain a membrane.

The cut-off molecular weight of the membrane was measured by cutting the membrane in a size of a diameter of 90 mm and equipping it with a ultrafiltration apparatus to measure retention percents of proteins of myoglobin (18,000), albumin (68,000), $\gamma$-globulin (160,000) and glutamate dehydrogenase (350,000). The cut-off molecular weight is about $3 \times 10^5$.

Human blood was treated by a centrifugal separation at low temperature to remove corpuscle components and to obtain blood plasma. pH of the blood plasma was adjusted to 8.0 with 1N-NaOH aqueous solution and 50% solution of polyethyleneglycol (4,000) was added to the blood plasma with cooling and stirring to give 12% of a concentration of polyethyleneglycol. The solution was treated by a centrifugal separation at low temperature and the supernatant was separated. pH of the supernatant was adjusted to 4.6 with 1N-HCl and polyethyleneglycol (4,000) flake was added to the solution with cooling and stirring to give 25% of a concentration of polyethyleneglycol. The mixture was treated by a centrifugal separation at low temperature to separate a precipitate. The precipitate was dissolved into a phosphate buffer solution having pH of 6.8 to prepare 1% solution. The solution was treated by an ultrafiltration under a pressure difference of 1 kg/cm$^2$ by an ultrafiltration apparatus equipped with the membrane.

Figure 2:
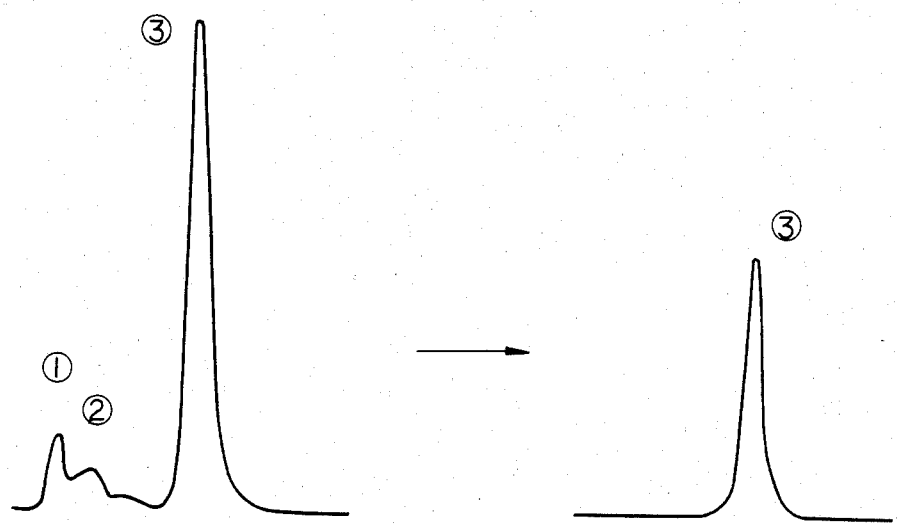
FIGS. 2 and 3 show the liquid chromatogram as the results of the examples of the present invention.

The chromatogram for the solution resulted under the following condition for measurement is shown in FIG. 2.

Condition of measurement

Gel permeation chromatography: HLC-802UR G3000SW (one column) manufactured by Toyo Soda Mfg. Co.

Eluent: phosphate buffer solution (pH 6.8)

Detector: UV monitor 280 nm

The chromatogram in the left side is that of the crude albumin fraction obtained by fractionation with polyethyleneglycol, before the ultrafiltration.

The chromatogram in the right side is that of the solution obtained by the ultrafiltration (plasma albumin). It is clear that only plasma albumin is permeated through the membrane according to the chromatogram. The permeation percent was about 50%.

Peaks (1) and (2): macromolecular proteins
Peak (3): plasma albumin.

EXAMPLE 2

The polysulfone resin of Example 1 was dissolved in a mixed solvent of N-methylpyrrolidone and dimethylsufoxide (7:3) to prepare 15% (W/V) solution. In accordance with the process of Example 1, an ultrafiltration membrane was prepared and a cut-off molecular weight of the membrane was measured. The cut-off molecular weight of the membrane was about $2.5 \times 10^5$. Human blood plasma was treated to give pH of 7.2, an ionic strength of 0.14, an ethanol concentration of 8% and a protein concentration of 5.1%, at $-3°$ C. and was further treated by a centrifugal separation to separate a supernatant. The supernatant was treated to given an ethanol concentration of 25%, pH of 6.9, an ionic strength of 0.09, a protein concentration of 3.0% at $-5°$ C. and further treated by a centrifugal separation to separate the supernatant ($S_{II+III}$ fraction). The supernatant was diluted to give a protein concentration of 1%. The solution was treated by the ultrafiltration as set forth in Example 1.

Figure 3:
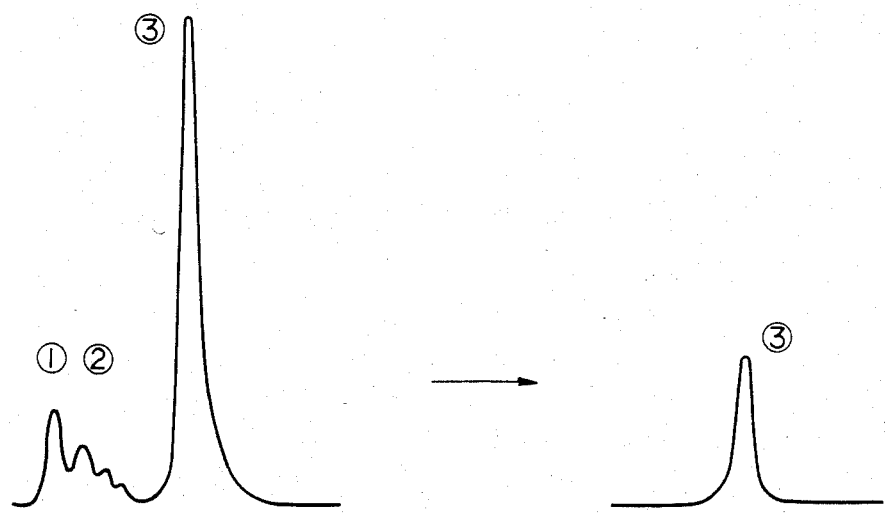

The chromatogram for the solution resulted under the condition of Example 1 is shown in FIG. 3.

It is clear that only plasma albumin is permeated through the membrane according to the chromatogram. The permeation percent was about 30%.

EXAMPLE 3

A polysulfone resin having the main unit;

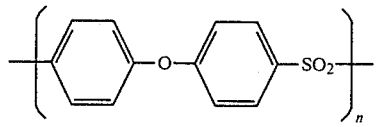

(n=150)
was dissolved into dimethylsulfoxide at a concentration of 15% (W/V). In accordance with the process of Example 1, an ultrafiltration membrane was prepared and a cut-off molecular weight of the membrane was measured. The cut-off molecular weight of the membrane was $3 \times 10^5$. Bovine blood was treated by the process of Example 1 with polyethyleneglycol to obtain rough plasma albumin fraction, and the fraction was treated by an ultrafiltration by a stirring type ultrafiltration apparatus equipped with the membrane as the process of Example 1. The chromatogram for the solution resulted is substantially the same as FIG. 3. It is clear that only albumin was filtered through the membrane. The permeation percent was about 30%.

REFERENCE 1

An ultrafiltration of human blood plasma having pH of 7 was carried out by using the membrane of Example 1. As a result, only small amount of plasma albumin was permeated by the ultrafiltration.

REFERENCE 2

In accordance with the process of Example 1 except using a commercially available cellulose acetate ultrafiltration membrane (cut-off molecular weight of $3 \times 10^5$) a fractionation and an ultrafiltration were carried out. As a result, a small amount of plasma albumin was permeated at the beginning but no plasma albumin was permeated later. The ultrafiltration rate was remarkably lowered.

We claim:

1. A process for purification of plasma albumin from crude fraction thereof which comprises separating a crude albumin fraction from blood plasma by a rough fractionation method and then separating plasma albumin in a purified fraction through an ultrafiltration membrane of a polysulfone resin having the formula:

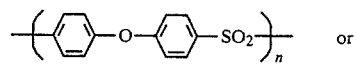

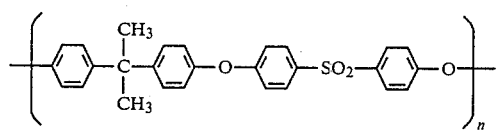

(n=50 to 250)

2. The process according to claim 1 wherein a fraction of the crude albumin separated from the blood plasma by the rough fractionation method using polyethyleneglycol is used.

3. The process according to claim 1 wherein a fraction of $S_{II+III}$ separated from the blood plasma by cohn cold ethanol fractional separation, is used.

4. The process according to claim 1, 2 or 3 wherein pH of an aqueous solution of the crude albumin is in a range of 5 to 8.

* * * * *